US012691208B2

(12) United States Patent
    Corazzari

(10) Patent No.: US 12,691,208 B2
(45) Date of Patent: Jul. 28, 2026

(54) FLUID COLLECTING CONTAINER

(71) Applicant: B. Braun Avitum AG, Melsungen (DE)

(72) Inventor: Enrico Corazzari, Mirandola (IT)

(73) Assignee: Braun Avitum AG, Melsungen (DE)

( * ) Notice: Subject to any disclaimer, the term of this patent is extended or adjusted under 35 U.S.C. 154(b) by 384 days.

(21) Appl. No.: 18/451,575

(22) Filed: Aug. 17, 2023

(65) Prior Publication Data

US 2024/0058517 A1 Feb. 22, 2024

(30) Foreign Application Priority Data

Aug. 18, 2022 (EP) ..................................... 22191058

(51) Int. Cl.
    *A61M 1/36* (2006.01)
(52) U.S. Cl.
    CPC ...... *A61M 1/36224* (2022.05); *A61M 1/3643* (2013.01)
(58) Field of Classification Search
    CPC .... A61M 1/3643; A61M 1/36224; A61J 1/10; A61J 1/1462; A61J 1/1475; A61J 1/20; A61J 1/2093
    See application file for complete search history.

(56) References Cited

U.S. PATENT DOCUMENTS

| | | | | | |
|---|---|---|---|---|---|
| 3,985,135 | A | * | 10/1976 | Carpenter | ................. A61J 1/10 604/410 |
| 4,432,763 | A | * | 2/1984 | Manschot | ................. A61J 1/10 222/456 |
| 5,431,496 | A | * | 7/1995 | Balteau | ............... A61M 1/1686 206/219 |
| 2013/0078144 | A1 | * | 3/2013 | Ishida | ................... A61J 1/1475 604/410 |
| 2019/0125952 | A1 | * | 5/2019 | Jansson | ............... A61M 1/1694 |

OTHER PUBLICATIONS

Search Report received in European Application No. 22 19 1058 dated Jan. 17, 2023, 4 pages.

* cited by examiner

*Primary Examiner* — Philip R Wiest

(74) *Attorney, Agent, or Firm* — Christopher A. Rothe; CM Law

(57) ABSTRACT

A fluid collecting container includes a fluid inlet, a fluid outlet, a front sheet and a back sheet. The front sheet and back sheet are fixed together at their edges and create a chamber in which the fluid can be collected. The fluid collecting container also has a channel having a first upper end fluidically connected to the fluid inlet and a second bottom end fluidically connected to the chamber. The channel is configured to increase the pressure drop at the fluid inlet once the fluid level in the chamber reaches the second bottom end.

18 Claims, 2 Drawing Sheets

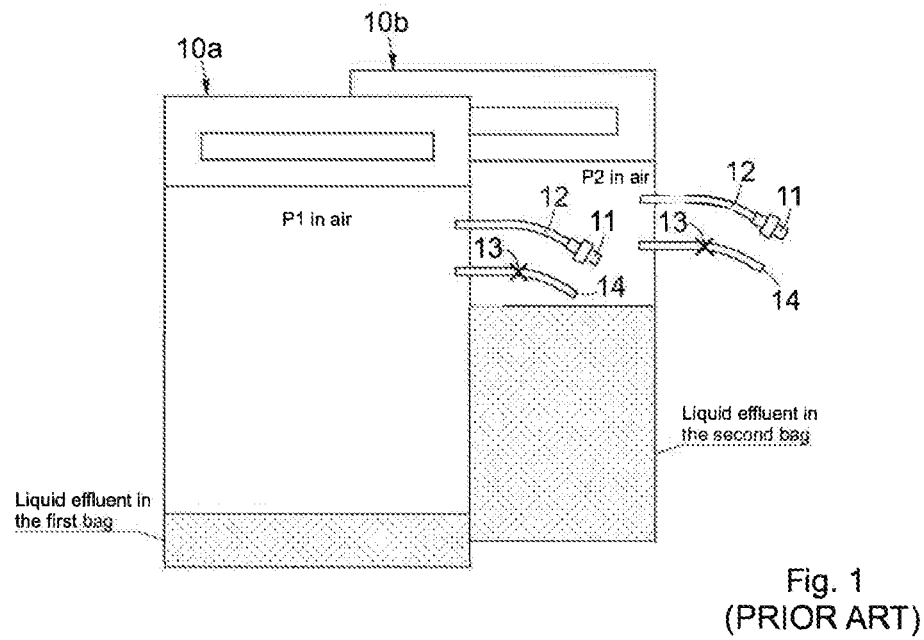
Fig. 1
(PRIOR ART)
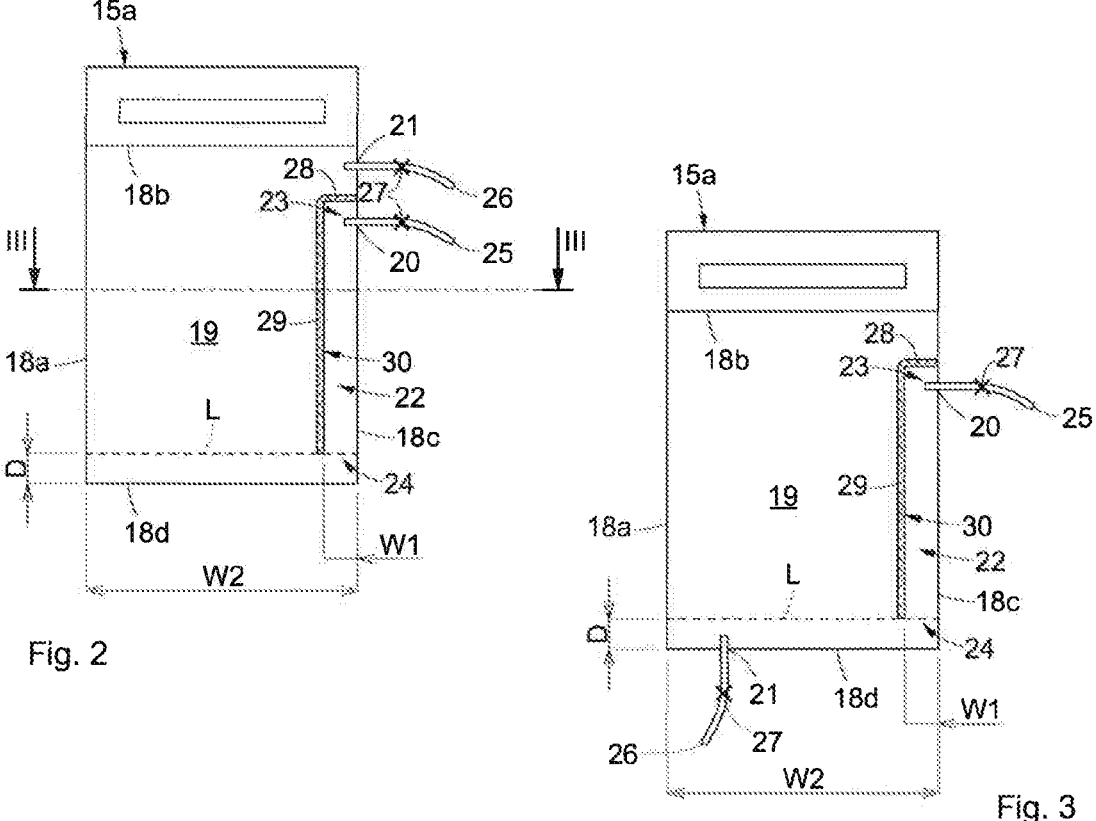
Fig. 2
Fig. 3

FLUID COLLECTING CONTAINER

CROSS-REFERENCE TO RELATED APPLICATIONS

This application claims priority under 35 U.S.C. § 119 to European Application No. 22 191 058.1, filed Aug. 18, 2022, the content of which is incorporated by reference herein in its entirety.

FIELD

The present disclosure concerns a fluid collecting container, in particular a self-levelling effluent container, for example in the form of a bag or pouch, that can be used in particular in all the applications where a plurality of fluid collecting containers that shall prime in parallel, so connected to the same liquid source, for example an extracorporeal blood treatment device.

BACKGROUND

In known machines or devices for extracorporeal blood treatment, waste fluid that accumulates during the treatment, for example blood treatment, is usually collected in one or more waste bags located on load cells of the machines.

The use for example of a couple of bags instead of one bag allows the operator to replace the full bags less frequently. One problem affecting this system is that sometimes one bag remains empty and the other become full when they are filled with liquid simultaneously and from the same source.

The problem related to said standard bags 10*a*, 10*b*, see for example FIG. 1 of the attached drawings, when primed in parallel using the same liquid source is that both the "in-air" side of bags are at the same pressure (P1=P2) since the beginning until the end of the priming. This means that the prevalence of the liquid is given solely by the difference in pressure drop of one bag with respect to the other. The differences in term of pressure drop, either localized in some zone of the bags or distributed along the piping, are caused, for example, by non-return valves 11 characteristics and other secondary effects such as the different adhesion of the sheets of which the bag is composed and the presence of more or less marked folds that change the characteristics in terms of resistance to filling.

Every bag 10*a*, 10*b* is provided with an inlet tube 12, in which it is positioned said non-return valve 11 and, and an outlet tube 14, in which a manual clamp 13 is positioned.

Another solution known in the art is given by the bags that are filled from the bottom. These bags solve the problem of not homogeneous filling since the two bags maintains the same level during priming.

However, filling bags from the bottom has some disadvantages for the following reasons:

the attachment for the tubes are uncomfortable to be reached by the operator every time they replace a filled bag;

it requires a longer tube for the connection with the machine instead of tube attachments on the upper side of the bags, as shown in the other solution herein above; and the attachments may interfere with the feet of the machine or with the floor so that the bags can rest at least partially on these external elements. This distorts the weight measure of the scale to which the bags are hung.

Examples of bags filled from the bottom are disclosed, for example, in patent documents US 2019/125952, U.S. Pat.

Nos. 3,985,135 and 5,431,496. The bag described in US 2019/125952 comprises an inlet passageway leading the fluid entering into the bag via the inlet connector to the corner of the bag opposite the side in which the inlet connector is placed. The bags described in U.S. Pat. Nos. 3,985,135 and 5,431,496 comprise at least one internal partition forming at least two separate chambers, which can be put in fluid communication when needed.

Another example of a similar bag comprising an internal partition is known also from US patent published under publication no. US 2013/078144, even if in this case the bags are filled from the side and not from the bottom.

None of these bags is able to ensure a self-levelling filling thereof.

SUMMARY

There is therefore a need to perfect a fluid collecting container, which can overcome at least one of the disadvantages of the state of the art.

In particular, one purpose of the present disclosure is to provide a fluid collecting container that allows it to be used in parallel with one or more other fluid collecting containers, with the certainty of priming them all substantially with the same liquid level.

Another purpose of the present disclosure is to provide fluid collecting container that can be efficiently utilized in medical fields, in particular, during extra corporeal treatments like dialysis to collect the waste liquid.

Another purpose of the present disclosure is to provide a simple and efficient method to collect fluid in a fluid collecting container.

Another purpose of the present disclosure is to provide an extracorporeal blood treatment device that uses at least a couple of fluid collecting containers.

The Applicant has devised, tested and embodied the present disclosure to overcome the shortcomings of the state of the art and to obtain these and other purposes and advantages.

In accordance with the above purposes, a fluid collecting container according to the present disclosure comprises a fluid inlet, a fluid outlet, a front sheet and a back sheet, which are fixed together at their edges and create a space in which the fluid can be collected.

According to one aspect of the disclosure, the fluid collecting container comprises a channel realized in said space, provided with a first upper end fluidically connected to said fluid inlet and a second bottom end fluidically connected to said space. Said channel is configured to increase the pressure drop at the fluid inlet once the fluid level in said space reaches said second bottom end.

Thanks to the provision of said channel, the pressure in the fluid inlet is increased until is greater than the sum of all the variables described above, that is non-return valve characteristics, adhesion of the sheets, the presence of marked folds due to packaging. Thus, in case of two fluid collecting containers connected in parallel to an extracorporeal blood treatment device, the fluid collecting containers can be filled equally and the liquid in them remain at the same level.

Thus, advantageously, the present fluid collecting container can be used in parallel with one or more other fluid collecting containers, with the certainty of priming them all substantially with the same liquid level.

The present fluid collecting container can thus be efficiently utilized in medical fields, in particular, during extra corporeal treatments like dialysis to collect the waste liquid.

According to a further aspect of the disclosure, the fluid collecting container is in the form of a bag or a pouch and realized in polyvinyl chloride (PVC) or other similar thermoplastic materials. For example, the fluid collecting container can be realized in polyethylene (PE), polyethylene terephthalate (PET), poly methyl methacrylate (PMMA), polypropylene (PP) or polyamide (PA). In possible embodiments, the fluid collecting container can be realized with combinations or blends of two or more of the thermoplastic materials listed above.

According to a further aspect of the disclosure, said fluid inlet is placed so as to lead the fluid in said collecting container directly inside said channel and said fluid outlet is located outside said channel.

According to a further aspect of the disclosure, said channel is formed by a lateral edge of said fluid collecting containers and by a weld that connects said front and back sheets.

According to a further aspect of the disclosure, said weld comprises a first weld part and a second weld part positioned such that the weld is substantially "L-shaped".

According to a further aspect of the disclosure, said first weld part is substantially horizontal, positioned above said fluid inlet and starting from said lateral edge of the fluid collecting container.

According to a further aspect of the disclosure, said second weld part is substantially vertical, starting from the end of the first weld part and its lower end defines said second bottom end of the channel.

According to a further aspect of the disclosure, said second weld part is substantially parallel to said lateral edge and thus the width of the channel is substantially constant.

According to a further aspect of the disclosure, a minimum distance between a bottom edge of the fluid collecting container and said second bottom end of the channel is defined that is dimensioned to allow the desired flowrate of the fluid from said channel toward said chamber. According to one possible embodiment, said minimum distance is substantially equal to the width of the channel.

According to a further aspect of the disclosure, the width of said channel is 5-25% of the width of the fluid collecting container.

According to a further aspect of the disclosure, the width of said channel corresponds to the length of said first weld part, said length being 5-25% of the length of the second weld part.

According to a further aspect of the disclosure, the maximum capacity of said chamber is comprised between 2 and 10 liters, preferably between 5 and 8 liters.

Another aspect of the disclosure is a method to collect fluid in a fluid collecting container, comprising a fluid inlet, a fluid outlet, a front sheet and a back sheet which are fixed together at their edges and create a chamber in which the fluid can be collected.

The method comprises:

the realization of a channel in said chamber, said channel comprising a first upper end fluidically connected to said fluid inlet and a second bottom end fluidically connected to said chamber;

leaving a minimum distance between a bottom edge of the fluid collecting container and said second bottom end of the channel, wherein said minimum distance is dimensioned to allow the desired flowrate of the fluid from said channel toward said chamber;

priming the fluid collecting container through said channel and increasing the pressure drop at the fluid inlet once the fluid level in said chamber reaches said second bottom end.

Another aspect of the disclosure is an extracorporeal blood treatment device, comprising at least a waste liquid discharge line and two or more fluid collecting containers connected in parallel to said waste liquid discharge line.

The present extracorporeal blood treatment device, advantageously, utilizes at least two fluid collecting containers in parallel that, thanks to the respective priming channels, are self-levelling such that the levels of the liquid in said fluid collecting containers are the same over time.

Thanks to the disclosure it is possible to achieve a homogeneous priming of the waste fluid amongst the two bags connected in parallel.

BRIEF DESCRIPTION OF THE DRAWINGS

These and other aspects, characteristics and advantages of the present disclosure will become apparent from the following description of some embodiments, given as a non-restrictive example with reference to the attached drawings, wherein:

FIG. 1 is a schematic front view related to two standard effluent bags known in the art;

FIG. 2 is a schematic front view of fluid collecting container according to the present disclosure;

FIG. 3 is a variant of the fluid collecting container of FIG. 2;

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION

We will now refer in detail to the possible embodiments of the disclosure, of which one or more examples are shown in the attached drawings. Each example is supplied by way of illustration of the disclosure and shall not be understood as a limitation thereof. For example, one or more characteristics shown or described insomuch as they are part of one embodiment can be varied or adopted on, or in association with, other embodiments to produce further embodiments. It is understood that the present disclosure shall include all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only and cannot be considered as limitative.

Figure 4:
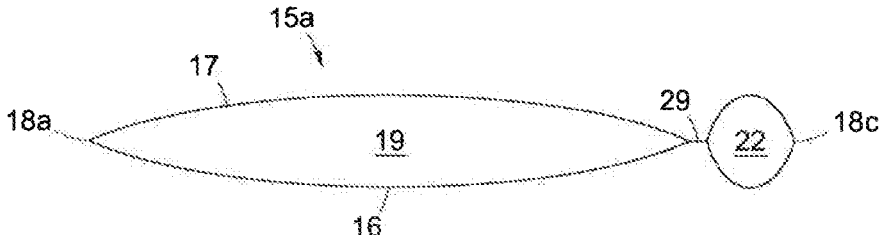
FIG. 4 is a section of the fluid collecting container taken along line III-III of FIG. 2.
Figure 5:
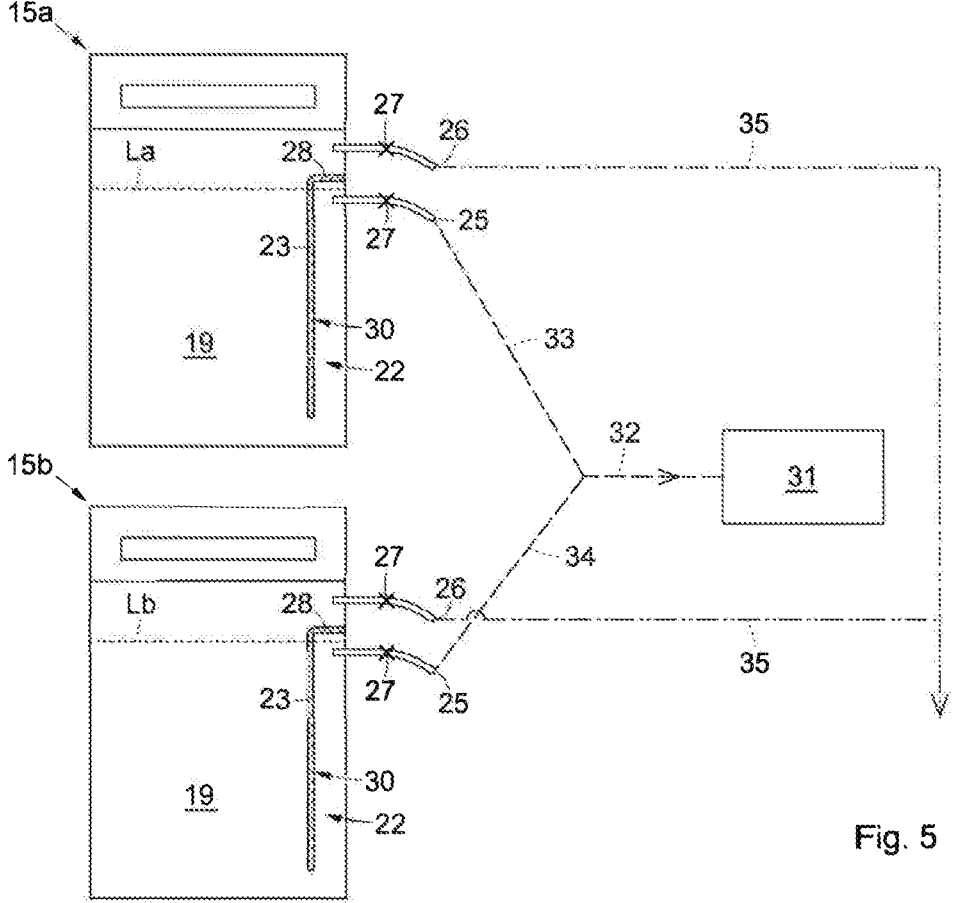
FIG. 5 is a schematic view of an extracorporeal blood treatment device according to the present disclosure.

With reference to the attached drawings, see for example FIGS. 2-4, a fluid collecting container 15a comprises a fluid inlet 20, a fluid outlet 21, a front sheet 16 and a back sheet 17. Said front and back sheets 16, 17 are fixed together at their edges 18a, 18b, 18c, 18d to create a chamber 19 in which the fluid can be collected. In particular, said edges comprises a left-lateral edge 18*a*, an upper edge 18*b*, a left-lateral edge 18*c* and a bottom edge 18*d*.

The maximum capacity of the chamber 19, when it is completely full, may range from 2 to 10 liters, more preferably from 5 to 8 liters, for example 7 liters.

The fluid collecting container 15*a* comprises at least a channel 22 made in said chamber 19.

The channel 22 comprises a first upper end 23 fluidically communicating with said fluid inlet 20 and a second bottom end 24 fluidically communicating with said chamber 19.

The fluid inlet 20 enters the fluid collecting container 15*a* at one of its lateral edges, in particular the right-lateral edge 18*c* in the examples shown in the figures.

The fluid inlet 20 leads the fluid inside the channel 22, preferably at its first upper end 23.

The channel 22 is configured to increase the pressure drop at the fluid inlet 20 once the fluid level L in said chamber 19 reaches said second bottom end 24.

The fluid collecting container 15*a* can be in the form of a bag or a pouch and be made in PVC (Polyvinyl chloride) or other similar flexible thermoplastic materials suitable to be used in medical field, such as for example PE, PET, PMMA, PP or PA.

The fluid inlet 20 and the fluid outlet 21 are fluidically communicating respectively with an inlet tube 25 and outlet tube 26 where respective manual clamps 27 are positioned.

The fluid inlet 20 is placed so as to lead the fluid entering the collecting container 15*a* directly inside the channel 22. The fluid outlet 21 is located outside said channel 22.

In the exemplary embodiment of FIG. 2, the fluid outlet 21 is located in the upper part of the fluid collecting container 15*a*, in particular above the fluid inlet 20. In the variant embodiment of FIG. 3, the fluid outlet 21 is located in the bottom part of the fluid collecting container 15*a*, at the bottom edge 18*d*. Preferably, the fluid outlet 21 near the lateral edge 18*a*, namely in the side of the container further from the channel 22 to avoid that the presence of the fluid outlet 21 may interfere with the filling of the collecting container 15*a* through the channel 22.

Said channel 22 is formed by a lateral edge 18*c* and by a first weld part 28 and a second weld part 29 that forms a substantially "L-shaped" weld 30. The weld 30 connects along said weld parts 28, 29 the front sheet 16 and the back sheet 17 of the fluid collecting container 15*a* leaving the channel 22 open at its second bottom end 24 communicating with the chamber 19.

The first weld part 28 is substantially horizontal, positioned above said fluid inlet 20 and starting from the lateral edge 18*c* of the fluid collecting container 15*a*. In other words, the first weld part 28 is located above the fluid inlet 20 forming a blind end of the channel 22 so that the fluid inlet 20 is forced to lead the fluid into the channel 22, from which the fluid reaches the chamber 19 passing through its second bottom end 24.

In another possible variant, the first weld part 28 can be inclined respect to a horizontal line, for example of an acute angle, up to 30°.

The second weld part 29 is substantially vertical, starting from the end of the first weld part 28 and its lower end defines said second bottom end 24 of the channel 22.

Said second weld part 29 is substantially parallel to said lateral edge 18*c* and thus the width W1 of the channel 22 is constant.

Said width W1 of the channel 22 can be 5-25% of the width W2 of the fluid collecting container 15*a*.

Between the bottom edge 18*d* of the fluid collecting container 15*a* and said second bottom end 24 of the channel 22 there is defined a minimum distance D, dimensioned to allow the desired flowrate of the fluid from the channel 22 toward the chamber 19.

In other words, the minimum distance D is the distance between the second weld part 29 and the bottom edge 18*b*.

In the examples shown in the figures attached, dimension D is substantially equal to the width W1 of the channel 22.

The width W1 of the channel 22 is basically defined by the length of the first weld part 28. Said length of the first weld part 28 can be 5-25% of the length of the second weld part 29.

In general, the minimum distance D should be wide enough to allow a proper filling of the chamber 19 to avoid any throttling that could hinder the fluid from passing from the channel 22 to the chamber 19.

Substantially, the weld 30 allows to create a closed channel 22 that increases the pressure drop in the inlet tube 25 once the liquid level L reaches the weld 30 itself, in particular the bottom end 24 of the channel 22. Due to the design of the weld 30 and thus of the channel 22, it is possible to ensure that the fluid collecting container 15*a* starts filling from the bottom side still maintaining the fluid inlet 20 in the upper part of the fluid collecting container 15*a*.

In FIG. 4 it is shown an extracorporeal blood treatment device 31, comprising for example a blood treatment unit, provided with at least two fluids collecting containers 15*a* and 15*b* connected in parallel to a waste liquid discharge line 32. The waste fluid discharge line 32 is divided into a first waste fluid discharge branch 33 connected to the fluid collecting container 15*a* and a second waste fluid discharge branch 34 connected to the fluid collecting container 15*b*. It should be noted that there may be additional branches and thus corresponding additional fluid collecting containers.

Flush lines 35 connects the outlet tubes 26 to any suitable waste disposal plant (not shown), for example comprising a reservoir or a sewerage. This allows to empties the fluid collecting containers 15*a*, 15*b* once they are filled up.

In the present fluid collecting container 15*a*, the pressure drops in the inlet tube 25 is increased until the pressure drop in each inlet tube 25 is greater than the pressure side effects generated by a sum of variables described above in the background section, for example non-return valve characteristics, adhesion of the sheets 16, 17, the presence of marked folds due to packaging.

The liquid is introduced in each fluid liquid container 15*a*, 15*b* through the inlet tube 25 and when the liquid level reaches the bottom end 24 of the channel 22, the pressure increases in said channel 22, increasing the pressure drop in said inlet tube.

With this pressure drop increasing, the liquid prevalence is due only to liquid level that creates a huge pressure on respect to the above secondary variables; this new concept has been tested by simulating the issue related to the standard design of the bags according to the following procedure:

connecting at least two fluids collecting containers 15*a* and 15*b* in parallel to a same liquid source, for example the extracorporeal blood treatment device 31;

clamping one of the two fluid collecting containers inlet tube 25; for example, clamping the inlet tube of the fluid collecting container 15*a;* starting the priming procedure of the other fluid collecting container 15*b* in which the inlet tube 25 is not clamped observing the behavior of the fluid collecting containers 15a and 15b once the clamp 27 of the inlet tube 25 of the fluid collecting container 15a is opened.

As a result, once the clamped fluid collecting container 15a is opened, it begins priming until the same liquid level of the other fluid collecting container 15b is reached, then both the fluid collecting containers 15a and 15b continue priming equally, thanks to the channel 22 realized in each fluid collecting container 15a, 15b. Thus, the levels La and Lb of the liquid in the fluid collecting containers 15a and 15b are the same and these latter containers 15a and 15b are thus filled homogeneously.

The present solution basically follows the Pascal principle which states that each variation of pressure in a closed recipient is transmitted equally to each part of the recipient and the liquid too.

Thus, self-levelling fluid collecting containers 15a, 15b are advantageously obtained and can be used in all the applications where two or more fluid collecting containers shall prime in parallel, so as to be connected to the same liquid source, for example an extracorporeal blood treatment device 31.

It is clear that modifications and/or additions of parts may be made to the fluid collecting container as described heretofore, without departing from the field and scope of the present disclosure.

It is also clear that, although the present disclosure has been described with reference to some specific examples, a person of skill in the art shall certainly be able to achieve many other equivalent forms of fluid collecting container.

What is claimed:

1. A fluid collecting container comprising:
a fluid inlet;
a fluid outlet;
a front sheet; and
a back sheet,
the front sheet and the back sheet being fixed together at edges, creating a chamber in which fluid is collectable, wherein the edges comprise a top edge, a bottom edge opposite the top edge, a first lateral edge joining the top edge with the bottom edge, and a second lateral edge opposite the first lateral edge joining the top edge with the bottom edge,
the fluid collecting container further comprising a channel having an upper end fluidically connected to the fluid inlet and a bottom end fluidically connected to a remainder of the chamber, wherein the channel extends along the first lateral edge, with the upper end and the fluid inlet located between the top edge and the bottom edge, and the bottom end spaced from and facing towards the bottom edge to thereby direct fluid exiting the channel into the remainder of the chamber towards the bottom edge,
the channel configured to increase a pressure drop at the fluid inlet when a fluid level in the chamber reaches the bottom end,
wherein a distance between the bottom edge of the fluid collecting container and the bottom end of the channel is dimensioned to allow a selected flowrate of the fluid from the channel toward the chamber.

2. The fluid collecting container according to claim 1, wherein the fluid collecting container is a bag or a pouch formed of thermoplastic material.

3. The fluid collecting container according to claim 1, wherein the fluid inlet is located so as to lead the fluid in the fluid collecting container directly inside the channel, and the fluid outlet is located outside the channel.

4. The fluid collecting container according to claim 1, wherein the channel is formed between the first lateral edge of the fluid collecting container and a weld that connects the front sheet and the back sheet.

5. The fluid collecting container according to claim 4, wherein the weld comprises a first weld part and a second weld part positioned relative to the first weld part such that the weld is L-shaped.

6. The fluid collecting container according to claim 5, wherein the first weld part extends from the first lateral edge towards the second lateral edge, and is positioned between the top edge and the fluid inlet.

7. The fluid collecting container according to claim 6, wherein the second weld part extends from an end of the first weld part towards the bottom edge to a lower end that defines the bottom end of the channel.

8. The fluid collecting container according to claim 7, wherein the second weld part is parallel to the first lateral edge, and a width of the channel is constant.

9. The fluid collecting container according to claim 8, wherein the width of the channel is 5-25% of a width of the fluid collecting container.

10. The fluid collecting container according to claim 8, wherein the width of the channel corresponds to a length of the first weld part, the length of the first weld part being 5-25% of a length of the second weld part.

11. The fluid collecting container according to claim 1, wherein the chamber has a maximum capacity of between 2 liters and 10 liters.

12. A method for collecting fluid in the fluid collecting container of claim 1 comprising the steps of:
priming the fluid collecting container through the channel; and
increasing the pressure drop at the fluid inlet when the fluid level in the chamber reaches the bottom end.

13. The fluid collecting container of claim 1, wherein the bottom end is oriented to direct fluid exiting the channel into a corner defined by an intersection of the first lateral edge and the bottom edge.

14. The fluid collecting container of claim 6, wherein the fluid inlet extends through the first lateral edge, and the fluid outlet extends through the first lateral edge and is positioned between the first weld part and the top edge.

15. The fluid collecting container of claim 8, wherein the first weld part is parallel to the top edge and perpendicular to the second weld part.

16. The fluid collecting container of claim 1, wherein the channel extends only along the first lateral edge.

17. An extracorporeal blood treatment device comprising:
at least two fluid collecting containers, wherein each of the at least two fluid collecting containers comprises:
a fluid inlet;
a fluid outlet;
a front sheet; and
a back sheet,
the front sheet and the back sheet being fixed together at edges, creating a chamber in which fluid is collectable,
a channel having an upper end fluidically connected to the fluid inlet and a bottom end fluidically connected to a remainder of the chamber, the channel configured to increase a pressure drop at the fluid inlet when a fluid level in the chamber reaches the bottom end, wherein a distance between a bottom edge of each fluid collecting container and the bottom end of the channel is dimensioned to allow a selected flow-rate of the fluid from the channel toward the chamber; and a waste liquid discharge line, the at least two fluid collecting containers being connected in a parallel fluid flow arrangement to said waste liquid discharge line.

18. The extracorporeal blood treatment device according to claim 17, wherein the respective fluid inlet of each of the at least two fluid collecting containers is fluidly connected to a waste liquid discharge line of the extracorporeal blood treatment device, and the respective fluid outlet of the at least two fluid collecting containers is connected to a waste disposal location that is fluidly separate from the waste liquid discharge line of the extracorporeal blood treatment device.

* * * * *